(12) United States Patent
Landry et al.

(10) Patent No.: US 7,556,600 B2
(45) Date of Patent: Jul. 7, 2009

(54) SURGICAL RETRACTION APPARATUS AND ASSOCIATED METHODS

(75) Inventors: Michael E. Landry, Fairfield, CT (US); Bruce A. Riceman, Leander, TX (US); Thomas A. Foster, Boulder, CO (US)

(73) Assignee: Zimmer Spine, Inc., Minneapolis, MN (US)

( * ) Notice: Subject to any disclaimer, the term of this patent is extended or adjusted under 35 U.S.C. 154(b) by 89 days.

(21) Appl. No.: 10/937,180

(22) Filed: Sep. 9, 2004

(65) Prior Publication Data

US 2006/0052672 A1    Mar. 9, 2006

(51) Int. Cl.
*A61B 1/32* (2006.01)
(52) U.S. Cl. .............................. 600/233; 600/231
(58) Field of Classification Search ................ 600/233, 600/231, 235, 224, 227–228, 201, 213, 214, 600/219, 232, 234
See application file for complete search history.

(56) References Cited

U.S. PATENT DOCUMENTS

| | | | | |
|---|---|---|---|---|
| 3,129,706 | A * | 4/1964 | Reynolds, Jr. | ............... 600/233 |
| 3,522,799 | A | 8/1970 | Gauthier | |
| 3,965,890 | A | 6/1976 | Gauthier | |
| 4,254,763 | A * | 3/1981 | McCready et al. | ........... 600/230 |
| 4,467,791 | A * | 8/1984 | Cabrera et al. | .............. 600/234 |
| 4,616,635 | A | 10/1986 | Caspar et al. | |
| 5,339,801 | A | 8/1994 | Poloyko et al. | |
| 5,503,617 | A | 4/1996 | Jako | |
| 5,520,608 | A * | 5/1996 | Cabrera et al. | .............. 600/201 |
| 5,580,344 | A | 12/1996 | Hasson | |
| 5,688,223 | A * | 11/1997 | Rosendahl | ................... 600/215 |
| 5,813,978 | A | 9/1998 | Jako | |
| 6,083,154 | A * | 7/2000 | Liu et al. | .................... 600/234 |
| 6,139,493 | A | 10/2000 | Koros et al. | |

(Continued)

FOREIGN PATENT DOCUMENTS

EP      1 090 589      4/2001

(Continued)

OTHER PUBLICATIONS

Maxcess Decompression Surgical Technique, Nuvasive, 2003, 16 pages.

(Continued)

*Primary Examiner*—Cris L Rodriguez
*Assistant Examiner*—Hao D Mai
(74) *Attorney, Agent, or Firm*—Crompton, Seager & Tufte, LLC.

(57) ABSTRACT

A retractor may be used during spinal surgery. The retractor may include a frame and one or more retractor blades. Each retractor blade may include a coupling arm, a retainer, and a retraction component. The coupling arms may be coupled to the frame such that the coupling arms are able to move inward or outwards relative to the frame. The retainer may secure the retraction component to the coupling arm. In some embodiments, the retraction blades may be made of a radiolucent material that allows radiological images to be taken during a surgical procedure with the retractor in place. A position of retraction components relative to the frame may be changed during a surgical procedure. One or more of the retraction components may be replaced during a surgical procedure without removing the retractor from the patient.

28 Claims, 3 Drawing Sheets

U.S. PATENT DOCUMENTS

| | | | |
|---|---|---|---|
| 6,206,828 B1 * | 3/2001 | Wright | 600/232 |
| 6,224,545 B1 | 5/2001 | Cocchia et al. | |
| 6,254,533 B1 * | 7/2001 | Fadem et al. | 600/208 |
| 6,421,659 B1 * | 7/2002 | Nomura | 707/3 |
| 6,464,634 B1 * | 10/2002 | Fraser | 600/233 |
| 6,530,883 B2 * | 3/2003 | Bookwalter et al. | 600/231 |
| 6,659,945 B2 | 12/2003 | Ball et al. | |
| 6,663,562 B2 | 12/2003 | Chang | |
| 6,679,833 B2 | 1/2004 | Smith et al. | |
| 6,712,795 B1 | 3/2004 | Cohen | |
| 6,723,043 B2 | 4/2004 | Kleeman et al. | |
| 6,849,064 B2 | 2/2005 | Hamada | |
| 6,945,933 B2 | 9/2005 | Branch et al. | |
| 2002/0022764 A1 | 2/2002 | Smith et al. | |
| 2002/0026101 A1 * | 2/2002 | Bookwalter et al. | 600/231 |
| 2003/0191371 A1 | 10/2003 | Smith et al. | |
| 2004/0087833 A1 | 5/2004 | Bauer et al. | |
| 2004/0176665 A1 | 9/2004 | Branch et al. | |
| 2005/0159650 A1 * | 7/2005 | Raymond et al. | 600/201 |
| 2005/0192485 A1 | 9/2005 | Branch et al. | |
| 2005/0215866 A1 * | 9/2005 | Kim | 600/233 |

FOREIGN PATENT DOCUMENTS

| | | |
|---|---|---|
| FR | 2 807 313 | 10/2001 |
| WO | 2004/006778 | 1/2004 |
| WO | 2004/047650 | 6/2004 |

OTHER PUBLICATIONS

Maxcess XLIF 90 Surgical Technique, Nuvasive, 2003, 28 pages.
Access Dilation Port, Spinal Concepts, Inc., Apr. 2003, 4 pages.
Leon J. Abram, M.D., "Dilation Discrctomy: A System for the Surgeon," Spinal Concepts, Inc. Jul. 2001, 4 pages.
Access Dilation Port, Spinal Concepts, Inc., 2001, 1 page.
PCT/US2005/031075 International Search Report, dated Jan. 19, 2006.

* cited by examiner

SURGICAL RETRACTION APPARATUS AND ASSOCIATED METHODS

BACKGROUND

1. Field of the Invention

The present invention generally relates to a surgical retraction instrument. More particularly, certain embodiments relate to a retractor for spinal surgery that allows for canted insertion of retraction components (blades) of the retractor and allows for independent movement of the retraction components.

2. Description of Related Art

A tissue retractor may be used during a surgical procedure to temporarily displace obstructing tissue and create a channel to a surgical target. The retractor may allow access to a surgical target while limiting an amount of dissection required to reach the surgical target. The retractor may be used to provide access to a spinal disc, a vertebra, and/or vertebrae during spinal surgery. The retractor may be used during minimally invasive spinal surgery.

A tissue retractor may include retractor components. Some of the retractor components, such as retractor blades, may be inserted into an incision made through a patient's skin. After insertion, a retraction mechanism may be engaged to increase a separation distance between retractor blades to retract tissue. Separation of the tissue by a retractor may allow a surgeon and/or surgical instruments unobstructed access to a site of interest while minimizing the requirement for dissection. Minimizing dissection may reduce tissue trauma, bleeding, recovery time, scarring, and patient risk that are associated with excessive dissection.

Retractor mechanisms that may be used in a surgical retractor instrument may include ratchet, screw or scissor mechanisms. Operation of the retractor mechanism may transmit force to retractor blades. The force separates the tissue into which the blades are inserted. Various retractors are disclosed in U.S. Pat. No. 6,712,795 to Cohen; U.S. Pat. No. 6,663,562 to Chang; U.S. Pat. No. 6,679,833 to Smith et al.; U.S. Pat. No. 6,659,945 to Ball et al.; U.S. Pat. No. 5,339,801 to Poloyko et al., each of which is incorporated by reference as though fully set forth herein.

Many retractors are composed of radio-opaque materials such as metal. The radio-opaque material may limit radiological imaging of a surgical site during a surgical procedure.

During some surgical procedures, it may be necessary to remove, exchange or replace one or more retractor components. Some retractors include blades that are fixed to a retractor mechanism. Some retractors include blades that cannot be removed and replaced while the retractor is in use. During some surgical procedures, the amount of retraction may need to be increased during a surgical procedure. Some retractors do not allow for extending an incision without completely releasing established retraction. During some surgical procedures, access to a surgical site from the skin of the patient may need to be made at an angle relative to the patient to allow for manipulation of tissue and/or insertion of an implant or stabilization system in a desired orientation. Some retractors cannot be easily canted so that excess separation with the retractor must be established to allow for manipulation of tissue and/or insertion of the implant or stabilization system in the desired orientation.

SUMMARY

A retractor may include a frame and a plurality of blades. The blades may include retraction components that retract tissue. In an embodiment, the retraction components may be independently coupled to the frame. The retraction components may be moved relative to the frame to establish or release retraction of tissue. In some embodiments, locking mechanisms may be coupled to the frame. A locking mechanism may fix or release a position of a blade. During a surgical procedure, a frame of a retractor may be coupled to a table arm or other stabilizer to fix a position of the retractor relative to the patient.

A blade of a retractor may include a coupling arm, a retainer and a retraction component. The coupling arm may be secured to a frame of the retractor such that the coupling arm is able to move inward or outward relative to the frame. The retainer may secure the retraction component to the coupling arm. The retractor component may be used to retract tissue to provide access to a surgical site. A retractor component may be removed from the retractor while the retractor is in use without removing the retractor from the patient. A different retractor blade may be secured to the retractor during the surgical procedure.

In some embodiments, the retractor may be made of a radiolucent material. In some embodiments, portions of the retractor (e.g., the frame) may be made of or include radio-opaque material, while other portions (e.g., the blades) may be made of a radiolucent material. In some embodiments, the radiolucent material may be carbon reinforced polymer. In some embodiments, the retractor may be made of material that can be thermally and/or chemically sterilized.

A retractor may be introduced into a patient. A frame of the retractor may be secured to a table arm to fix the position of the frame relative to the patient. Retraction components of the retractor may be moved to retract tissue and provide access to a surgical site. When desired, the retraction components may be released to remove established retraction.

In an embodiment, the retractor may be angled during a surgical procedure. Angling the retractor during a surgical procedure may allow a surgeon to displace the retraction components such that the retraction components are moved to a nearby or adjacent surgical site. The retractor may be angled during a surgical procedure without requiring removal of the retraction instrument and/or extension of the incision in the patient.

One or more retraction components may include a slot. The slot may allow extension of an incision in the patient without the need to remove the retractor and/or release retraction of tissue.

BRIEF DESCRIPTION OF THE DRAWINGS

Advantages of the invention will become apparent to those skilled in the art with the benefit of the following detailed description of embodiments and upon reference to the accompanying drawings in which.

Figure 1:
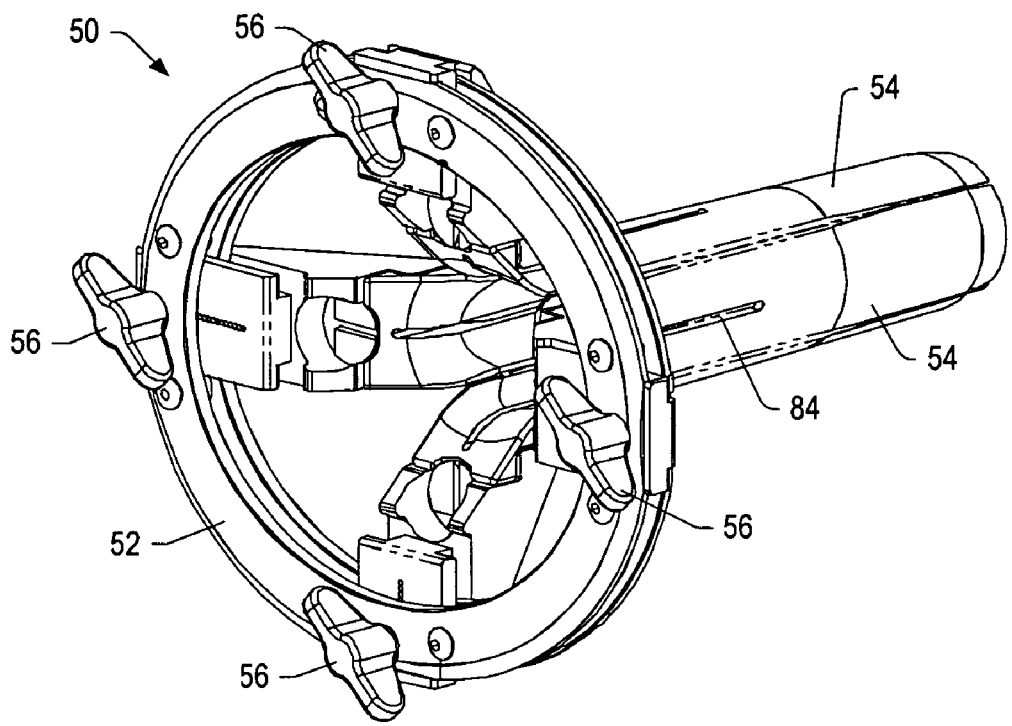
FIG. 1 depicts a perspective view of an embodiment of a retractor.

While the invention is susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims.

DETAILED DESCRIPTION

Referring to the drawings, and more particularly to FIG. 1, a retractor is indicated generally by reference numeral 50. Retractor 50 may be used during a surgical procedure to temporarily displace obstructing tissue and create a channel to gain access to a surgical target. Retractor 50 may be used to retract or otherwise displace skin, muscle tissue, organs, bone, blood vessels, connective tissue, nerve tissue or the like. Retractor 50 may include frame 52, blades 54, and locking mechanisms 56. Blades 54 may be fixed in position relative to frame 52 by locking mechanisms 56.

Retractor 50 may be made of materials that allow the retractor to be heat and/or chemically sterilized. Components of the retractor may be made of metal, ceramics and/or polymers. In some retractor embodiments, the retractor may be made of radiolucent material. In some embodiments, the blades or components of the blades may be formed of a radiolucent material. The radiolucent material may allow radiological imaging of a surgical site while the retractor is in use. In some embodiments, the radiolucent material may be a polymer or a carbon-reinforced polymer. In some embodiments, the polymer may be polyetheretherketone (PEEK). In some embodiments, radio-opaque markers may be placed at selected locations in the retractor. For example, a tantalum bead may be positioned at or near the end of a blade so that the position of the blade is indicated in radiological images taken during a surgical procedure. Radio-opaque markers may be positioned in the frame and/or in one or more of the blades. In some embodiments, a portion of a blade formed of a polymeric material may include radio-opaque material (e.g., barium doping) so that a position of the blade is indicated on radiological images taken during a surgical procedure.

Figure 2:
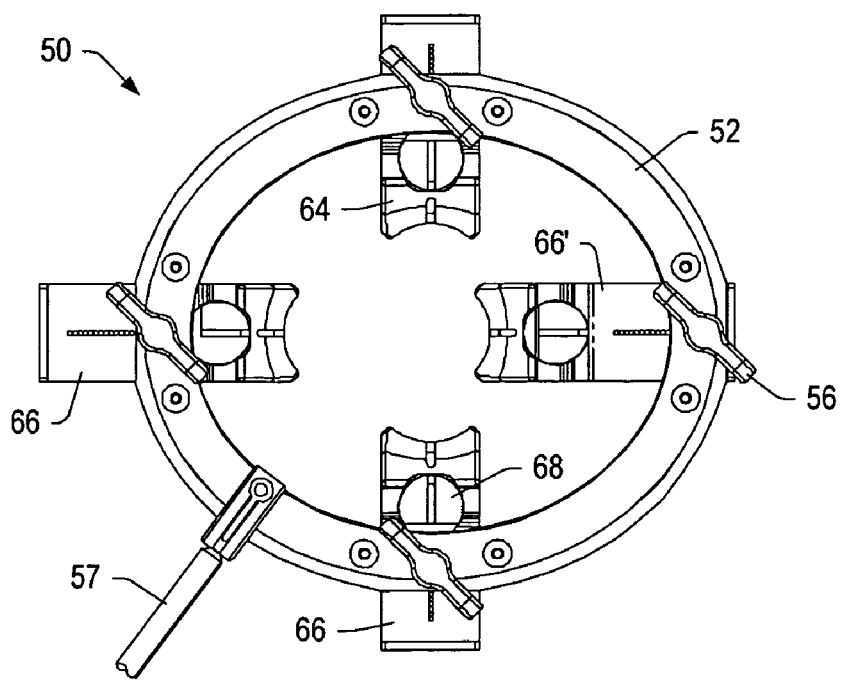
FIG. 2 depicts a top view of an embodiment of a retractor.

FIG. 2 depicts a top view of retractor 50. Interior perimeter of frame 52 may establish a work area. The interior perimeter of frame 52 may have, but is not limited to having, an elliptical, oval, circular, or rectangular shape. In some embodiments, the interior perimeter of frame 52 may have a shape with a major axis and a minor axis. For example, a frame with an elliptical interior perimeter (such as the frame depicted in FIG. 2) has a major axis and a minor axis. The major axis may be aligned in a desired orientation relative to the patient prior to fixing the position of retractor 50 using table arm 57. During some spinal surgery procedures, the major axis of the frame may be oriented in cephalad-caudal direction.

During some surgical procedures, frame 52 may be secured to table arm 57. Table arm 57 may fix the position of frame 52 relative to a surgical table and a patient. In some embodiments, frame 52 may provide a structure that instruments are attached to. The instruments may be, but are not limited to, light sources, suction tubes, retractors, scissors, and/or imaging devices (e.g., laparoscopes). In some embodiments, the instruments may be positioned through one or more openings formed in the frame. In some embodiments, the instruments may be clamped, screwed, or otherwise attached to the frame.

Figure 3:
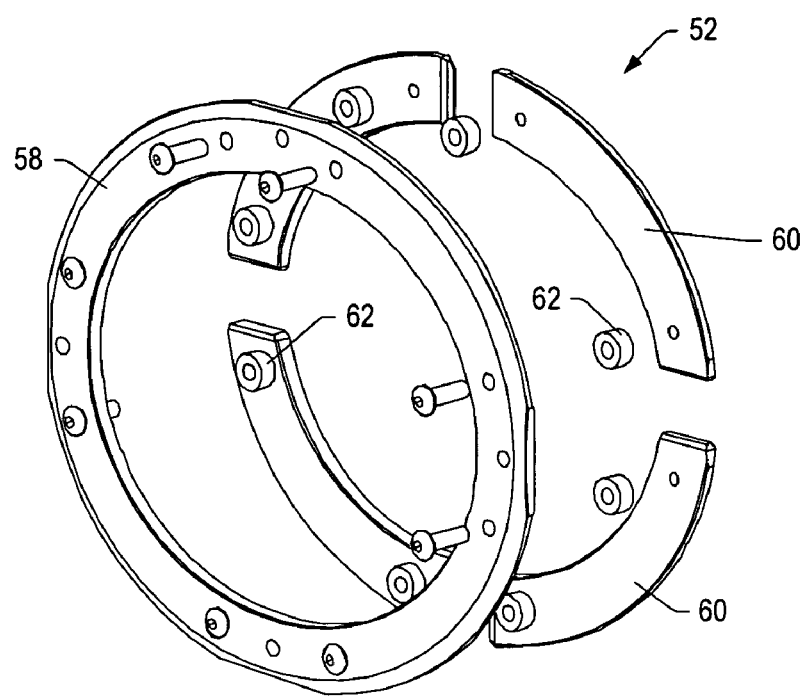
FIG. 3 depicts an expanded perspective view of an embodiment of a frame of a retractor.

In some embodiments, a frame of a retractor may be formed of a single piece of material. Slots may be formed in the frame to allow blades to be inserted into the frame. In some embodiments, a frame of a retractor may be formed from several pieces. FIG. 3 depicts an expanded perspective view of an embodiment of frame 52. Frame 52 may include upper portion 58, segments 60 and spacers 62. Spacers 62 may establish a separation distance between upper portion 58 and segments 60 that allows a blade to be inserted into frame 52. Spacers 62 may be held in position by epoxy or other adhesive, welds, rivets, screws, and/or other fastening systems. The distance established by spacers 62 between upper portion 58 and segments 60 allows blades inserted in frame 52 to be moved relative to the frame to retract tissue or to release established retraction. When a blade is retracting tissue, force applied by the tissue to the blade may apply a moment to the blade that binds frame 52 and the blade together. The binding of the blade relative to frame 52 may inhibit movement of the blade relative to the frame when a force used to cause additional retraction is removed.

In addition to a binding force between a blade and a frame, a locking mechanism may be used to secure the position of a blade relative to a frame. As shown in FIG. 1, retractor 50 may include locking mechanisms 56 for each blade 54. Locking mechanism 56 may lock the position of blade 54 relative to frame 52 to insure that the binding of the frame and blade is not unintentionally released. When release of retraction established by blade 54 is desired, or when additional retraction is desired, locking mechanism 56 may be released. A moment may then be applied to blade 54 that counteracts the moment applied by the blade to frame 52 caused by the retracted tissue. Blade 54 may then be moved relative to frame 52.

A frame may hold a selected number of blades. A frame may hold two, three, four, five, six, or more blades. For example, the retractor embodiment depicted in FIG. 1 is designed to hold four blades. During some surgical procedures, less than the maximum number of blades that the frame can hold may be used. For example, a frame designed to hold 6 blades may be used with 3 blades.

Figures 4, 5:
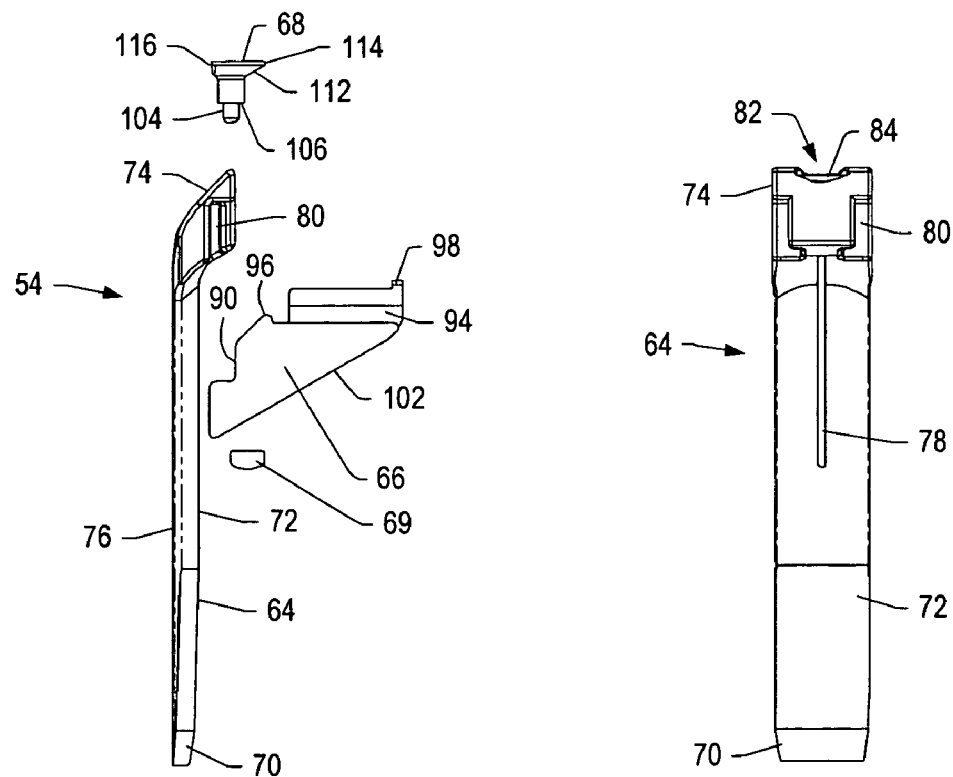
FIG. 4 depicts an expanded view of a blade for a retractor.
FIG. 5 depicts a plan view of an embodiment of a retraction component of a blade.

In some embodiments, blades of a retractor may be formed as a single, unitary piece of material. In some embodiments, a blade may be formed of a number of components. FIG. 4 depicts an expanded view of an embodiment of blade 54 formed of three components. Blade 54 may include retraction component 64, coupling arm 66, retainer 68, and fastener 69.

Retraction component 64 may be releasably attached to coupling arm 66 by retainer 68. Fastener 69 may be coupled to retainer 68 to inhibit separation of the retainer from coupling arm 66.

Retraction component 64 may include tip 70, body 72 and head 74. Tip 70 may be tapered to facilitate insertion of retraction component 64 into a patient. Tip 70 and body 72 may be curved. Inner surface 76 may have a curvature that is substantially complementary to a curvature of a large distractor or instrument that is used to provide initial access to a surgical site.

FIG. 5 depicts a plan view of an embodiment of retraction component 64. In some embodiments, body 72 may include slot 78. During a surgical procedure using a retractor, a scalpel or other cutting instrument may be used through slot 78 to extend an incision in a patient during the surgical procedure. Advantageously, the incision in the patient may be extended without removing the retractor from the patient.

Head 74 of retraction component 64 may include one or more grooves 80 and retainer recess 82. Grooves 80 may be complementary to recesses in the coupling arm of the blade. Retainer recess 82 may include frusto-conical surface 84 that complements a frusto-conical surface of a retainer used to secure retraction component 64 to a coupling arm.

An instrument set for a surgical procedure may include a number of retraction components of various lengths. Lengths of retraction components may generally be from about 20 mm to about 200 mm, though retraction components may be shorter or longer than these lengths. Retraction components for posterior spinal approaches may range in length from about 20 mm to about 80 mm. Retraction components for anterior spinal approaches or lateral spinal approaches may range in length from about 70 mm to about 200 mm.

Figure 6:
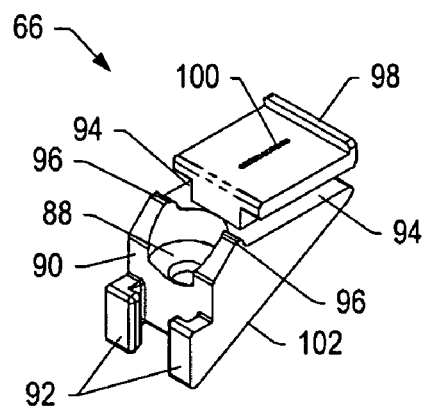
FIG. 6 depicts a perspective view of an embodiment of a coupling arm.

FIGS. 4 and 6 depict an embodiment of coupling arm 66. Coupling arm 66 may include retainer port 88, retainer port edge 90, retraction component protrusions 92, frame grooves 94, inner stop 96, outer stop 98, depressions 100 and sloped surface 102. Retainer port 88 may be an opening through the body of coupling arm 66. A retainer may be positioned in retainer port 88. When a straight edge of the retainer is aligned with retainer port edge 90, a retraction component may be coupled to or released from coupling arm 66.

Protrusions 92 on coupling arm 66 may complement the grooves in a retraction component. When the retraction component is coupled to coupling arm 66, interaction of protrusions 92 and the grooves of the retraction component may inhibit lateral movement and rotation of the retraction component relative to the coupling arm.

Frame grooves 94 of coupling arm 66 may complement a portion of a frame so that the coupling arm may be moved into or out of the frame. In an embodiment, end portions of segments of the frame may fit in frame grooves 94. Inner stop 96 and outer stop 98 may inhibit separation of a blade from a frame of a retractor. When coupling arm 66 is positioned in the frame, contact of inner stop 96 with segments of the frame may limit a range of outward movement of the coupling arm relative to the frame. When coupling arm 66 is positioned in the frame, contact of outer stop 98 with the upper portion of the frame may limit a range of inward movement of the coupling arm relative to the frame.

Depressions 100 may be located on an upper surface of coupling arm 66. A tip of a locking mechanism may be placed in one of depressions 100. In some embodiments, a locking mechanism may include a threaded portion that mates with threads in openings through an upper portion of a frame. In some embodiments, rotating the locking mechanism in a clockwise direction may extend a tip of the locking mechanism into one of depressions 100. When the tip of the locking mechanism is located in one of depressions 100, the locking mechanism may inhibit unintentional movement of coupling arm 66 relative to the frame. Rotating the locking mechanism in a counterclockwise direction may retract the tip of the locking mechanism from depression 100 and allow movement of coupling arm 66 relative to the frame. In some embodiments, a locking mechanism may be coupled to the frame by a spring system that extends the tip of the locking mechanism into depressions 100. In some embodiments, a head of the locking mechanism may include, or may be, an indicator that reveals to a user if the locking mechanism is extended into depression 100.

Coupling arm 66 may include sloped surface 102. A force may be applied to sloped surface to counteract a moment that binds coupling arm 66 to a frame of a retractor. Sloped surface 102 may inhibit contact of the frame with the patient. Sloped surface 102 may facilitate positioning a retractor at an angle in a patient. In some embodiments, the retractor may be positioned at an angle to allow access to a surgical site at a desired angle. In some embodiments, the retractor may be angled to gain access to a secondary surgical site that is near or adjacent to a primary surgical site without requiring removal of the retractor from the surgical incision.

Figure 7:
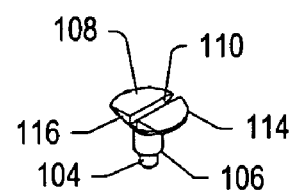
FIG. 7 depicts a perspective view of an embodiment of a retainer.

FIGS. 4 and 7 depict an embodiment of retainer 68. In some embodiments, retainer 68 may be a cam that engages a retraction component to secure the retraction component to a coupling arm. Retainer 68 may include end 104, stop 106, and head 108. Retainer 68 may be positioned in retainer part of a coupling arm. Fastener 69 may be coupled to end 104 to secure retainer 68 in the retainer port. Stop 106 may fix a position of fastener 69 relative to retainer 68 and relative to a coupling arm. In some embodiments, end 104 may include thread that mate with thread of fastener 69. In some embodiments, fastener 69 may be glued, welded, sonically welded, or otherwise fixed to end 104 to inhibit separation of the fastener from retainer 68.

In some embodiments, retainer may be a spring lock mechanism. Spring arms may be compressed when the retainer is pushed through the retainer port. When stops on the spring arms pass beyond an end of the retainer port, the spring arms may expand outwards. The stops on the spring arms may inhibit removal of the retainer from the retainer port.

In some embodiments, retainer may be a threaded member. A shaft of the threaded member may be positioned through an opening in a coupling arm. A threaded portion of the shaft may engage a complementary thread in a retraction component to secure the retraction component to the coupling arm.

Head 108 of retainer 68 may include tool port 110, frusto-conical surface 112, curved edge 114, and straight edge 116. When retainer 68 is positioned in a retainer port of a coupling arm, a tool (e.g., a screwdriver) may be inserted into tool port 110. The tool may be used to rotate retainer 68. When retainer 68 is to secure a retraction component to a coupling arm, retainer 68 may be rotated so that straight edge 116 is aligned parallel and near to a retainer port edge of the coupling arm. When straight edge 116 is aligned parallel and near to the retainer port edge, the retraction component may be moved relative to the coupling arm so that retraction component protrusions are positioned in grooves of the retraction component. Retainer 68 may be rotated so that frusto-conical surface 112 of the retainer engages a frusto-conical surface of the retraction component. Engaging frusto-conical surface 112 of retainer 68 with the frusto-conical surface of the retraction component may apply an outward and downward force to the retraction component that securely couples the retraction component to the coupling arm. When the frusto-conical surface 112 of retainer 68 is used to couple the retraction component to the coupling arm, the retainer may be rotated so that curved edge 114 extends over the retraction component and straight edge 116 is substantially parallel to the retainer port edge.

When a retraction component is to be removed from a coupling arm, the retainer may be rotated so that curved edge 114 does not extend over the retraction component. The retraction component may then be grasped and removed from the coupling arm. Retainer 68, depicted in FIG. 2, is shown in an unlocked position such that retraction component 64 can be removed from coupling arm 66.

A retractor may be provided in an instrument set for a surgical procedure. The instrument set may include one or more frames with coupling arms positioned in each frame. Inner stops and outer stops of the coupling arms may inhibit separation of the coupling arms from the frame. The coupling arms included in the instrument set may have retainers positioned in the retainer ports. The instrument set may also include a plurality of retraction components. The retraction components may be of various lengths. In some embodiments, the instrument set may include a set of retraction components for each coupling member in a frame. Each set of retraction components may include, for example, 10 retraction components ranging in length from a smallest retraction component to a largest retraction component in 5 mm increments.

Some spinal surgery procedures may be minimally invasive surgical procedures where an incision in the patient is maintained as small as possible. Some of the instruments used during a minimally invasive procedure may establish tissue distraction during the minimally invasive procedure. During some minimally invasive procedures, operating conditions may necessitate retraction during the surgical procedure. The retraction may allow visibility of areas adjacent to a surgical site in the patient and/or may provide additional needed working space needed for manipulation and/or orientation of surgical instruments. The retractor described herein may be used to provide retraction during a minimally invasive surgical procedure.

During a surgical procedure, an initial incision may be made through the skin of a patient. A series of dilators may be used to initially distract tissue from the incision to a surgical site. The dilators may be cylindrical tubes of increasing diameter. One or more of the dilators may include side markings that indicate a depth of insertion of the dilators. The markings on the dilator may be used to choose lengths of retraction components to attach to a retractor. Retraction components of desired lengths may be secured to coupling arms using retainers. The retraction components may be positioned about a dilator. A curvature of inner surfaces of the retraction components may be complementary to the curvature of the dilator. When the retraction components are positioned against the dilator, the position of the retraction components relative to the frame may be secured by tightening locking mechanisms. The retraction components may be moved downwards through the incision. When the retraction components are fully inserted in the patient, the dilator may be removed.

A table arm may be coupled to the frame. In some embodiments, the table arm may be coupled to the frame before the dilator is removed from the patient. The table arm may include a clamp that locks to the frame. In some embodiments, the table arm may include one or more protrusions that mate with one or more openings in the frame. The table arm may fix the position of the retractor relative to the table and relative to the patient. The frame may be positioned so that the frame does not contact the patient.

To retract tissue, a first locking mechanism may be loosened to free a first coupling arm relative to the frame. Retraction force may be applied to the coupling arm to move the retraction component outwards relative to the frame. In some embodiments, the retraction force may be applied to the coupling arm by force applied by a hand of a surgeon. In some embodiments, retraction force may be applied by an instrument. A first arm of the instrument may be placed in the retainer port. A second arm of the instrument may contact an outer edge of the frame on both sides of the coupling arm. Retraction force may be applied to the first arm and the second arm to move the first arm towards the second arm. When application of the retraction force is stopped, the tissue being retracted may apply a force against the retraction component. The force applied by the tissue may cause a moment that binds the coupling arm against the frame. The binding between the coupling arm and the frame may inhibit movement of the coupling arm relative to the frame. The remaining locking mechanisms may be loosened sequentially and retracting forces may be applied to the corresponding coupling arms and retraction components to achieve retraction. When the desired amount of retraction has been obtained, locking mechanisms may be tightened to secure the positions of the coupling arms relative to the frame.

During some surgical procedures, an initial incision made through the skin may be too small. One or more of the retraction components may include a slot. A scalpel or other cutting instrument may be used through the slot to extend the incision without the need to release established retraction and/or remove the retractor or retraction components from the patient. After the incision is extended, additional retraction may be established by releasing the locking mechanism for the coupling arm and retraction component that are to be moved. Retraction force may be applied to the coupling arm to establish additional retraction. Application of the retraction force may be stopped, and the locking mechanism may be tightened to secure the position of the retraction component relative to the frame.

During some surgical procedures, an initial retraction component may need to be removed, replaced or exchanged with a different (longer or shorter) retraction component. A locking mechanism that secures the position of the retraction component to be removed, replaced or exchanged may be released. Force may be applied to the retraction component to release established retraction. In some embodiments, additional retractors may be coupled to the frame to hold tissue in a retracted state while the retraction component is replaced. Force applied to release established retraction may include a counteracting moment to the moment that binds the coupling arm to the frame. The counteracting moment may be generated by applying force to the sloped surface of the coupling arm. The force applied to release established retraction may be applied by hand or by an instrument. The instrument may include a first arm that contacts the sloped surface of the coupling arm. The instrument may also include a second arm that couples to an inner surface of the frame on both sides of the retraction component that is to be replaced. The first arm may be moved towards the second arm to release retraction.

When retraction applied by the retraction component to be replaced is relieved, the retainer may be rotated to a position that allows the retraction component to be removed from the coupling arm. The retraction component may be removed from the coupling arm, and the replacement retraction component may be placed on the coupling arm. The retainer may be rotated to secure the replacement retraction component to the coupling arm. The replacement retraction component may be used to establish retraction of adjacent tissue.

Figure 8:
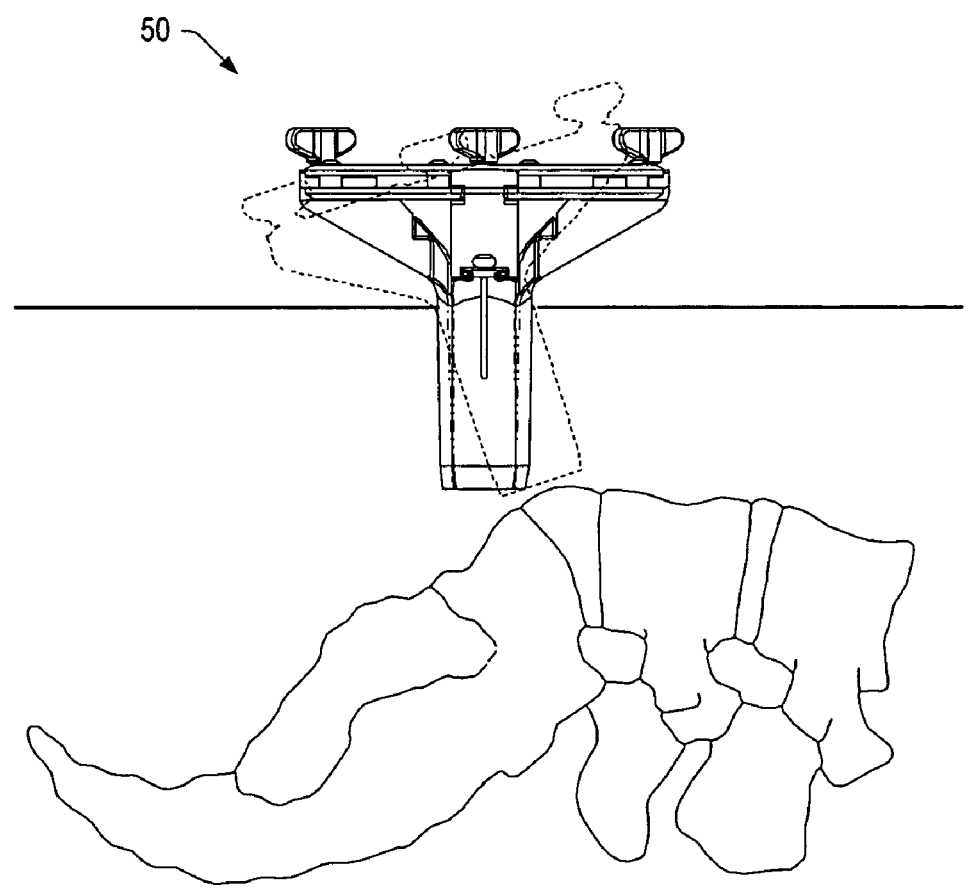
FIG. 8 depicts a cross sectional view of a surgical retraction apparatus in use, and includes a depiction of "wanding allowance."

During some surgical procedures, retraction may need to be adjusted to allow access to a surgical site from a desired angle. A sloped surface of a coupling arm may allow a retractor to be angled during a surgical procedure without the need to remove the retractor from the patient. FIG. 8 depicts a schematic representation of retractor 50 before (solid lines) and after (dotted lines) the retractor is angled. If needed, a table arm may be adjusted to change the lateral position of the retractor before, during or after angling the retractor. In some embodiments, angling the retractor may necessitate changing one or more of the retraction components of the retractor. In some embodiments, a retractor may be initially introduced into the patient at an angle instead of being angled during the surgical procedure.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A human spinal surgical retraction apparatus, comprising:
    a plurality of blades;
    a retainer with a straight edge; and
    a frame with an opening and includes an upper portion, spacers, and segments,
        wherein a separation distance established by the spacers between the upper portion and the segments allows a selected number of blades to be inserted into the frame, and
        wherein each of the plurality of blades includes:
            a coupling arm comprising frame grooves, a sloped surface, and retraction component protrusions, wherein the frame grooves complement a portion of the frame to allow the coupling arm to be moved into or out of the frame; and
            a retraction component comprising a head and a body, wherein the head of the retraction component includes one or more grooves for releasably coupling the retraction component to the retraction component protrusions of the coupling arm,
            wherein when the retraction component is coupled to the coupling arm, interaction of the retraction component protrusions of the coupling arm and the one or more grooves of the retraction component inhibits lateral movement and rotation of the retraction component relative to the coupling arm,
            wherein the body of the retraction component of at least one of the plurality of blades includes a slot through which a surgical instrument is acceptable,
            wherein the coupling arm further comprises a retainer port and a retainer port edge,
            wherein the retainer is acceptable by the retainer port of the coupling arm, and
            wherein when the straight edge of the retainer is aligned with the retainer port edge of the coupling arm, the retraction component is releasable from the coupling arm.

2. The apparatus of claim 1, wherein the plurality of blades has retraction components of varying lengths.

3. The apparatus of claim 1, further comprising locking mechanisms, wherein the plurality of blades are fixed in position relative to the frame by the locking mechanisms.

4. The apparatus of claim 1, wherein the retraction component has a length from about 30 mm to about 130 mm.

5. The apparatus of claim 1, wherein the apparatus comprises radiolucent material.

6. The apparatus of claim 1, wherein the surgical instrument is a cutting instrument and wherein the slot allows the cutting instrument to pass through to extend an incision in a patient without removing the apparatus from the patient.

7. The apparatus of claim 6, wherein the surgical instrument is a scalpel.

8. The apparatus of claim 1, wherein the frame is configured to lie in a plane that is above the plane of the human spinal surgical opening.

9. The apparatus of claim 1, wherein the coupling arm is configured to cause the frame to lie in a plane that is above the plane of the human spinal surgical opening.

10. The apparatus of claim 1, wherein a side of the coupling arm is configured to be substantially non-parallel to the plane of the human spinal surgical opening.

11. The apparatus of claim 1, further comprising a stabilizing device configured to couple to the frame, wherein the stabilizing device inhibits movement of the frame during use.

12. A human spinal surgical apparatus, comprising:
    a frame with an opening, wherein the frame is configured to be moveably angled relative to the human spinal surgical opening; and
    a plurality of blades, wherein each of the plurality of blades comprises:
        a coupling arm configured to be coupled to the frame, said coupling arm comprising a protrusion, a retainer port, a retainer port edge, and a sloped surface;
        a retainer with a straight edge; and
        a retraction component configured to retract tissue in the human spinal surgical opening, said retraction component comprising a groove and a slot,
        wherein the groove slidably engages the protrusion for coupling the retraction component to the coupling arm,
        wherein the retainer is acceptable by the retainer port of the coupling arm,
        wherein when the straight edge of the retainer is aligned with the retainer port edge of the coupling arm, the retraction component is releasable from the coupling arm,
        wherein when the retraction component is coupled to the coupling arm, interaction of the protrusion and the groove inhibits lateral movement and rotation of the retraction component relative to the coupling arm,
        wherein the slot of said retraction component provides a surgical instrument with access to the human spinal surgical opening, and
        wherein when the retraction component is at least partially inserted in tissue, the retraction component can be decoupled from the coupling arm and frame by pulling the retraction component substantially out of an incision and substantially perpendicular to the frame opening.

13. The apparatus of claim 12, wherein the retraction component is configured to be independently removable while in the human spinal surgical opening.

14. The apparatus of claim 12, wherein the retraction component is configured to be independently replaceable while in the human spinal surgical opening.

15. The apparatus of claim 12, wherein the retraction component has a length of about 30 mm to about 130 mm.

16. The apparatus of claim 12, wherein the apparatus comprises radiolucent material.

17. The apparatus of claim 12, wherein the coupling arm is configured to be moveably coupled to the frame.

18. The apparatus of claim 12, wherein applying a force to the retraction component moves the retraction component in the direction of the applied force.

19. The apparatus of claim 12, wherein the retraction component comprises an opening, wherein the opening is configured to accept a surgical instrument.

20. The apparatus of claim 19, wherein the surgical instrument is a scalpel.

21. The apparatus of claim 12, wherein the frame is configured to lie in a plane that is above the plane of the human spinal surgical opening.

22. The apparatus of claim 12, wherein the coupling arm is configured to cause the frame to lie in a plane that is above the plane of the human spinal surgical opening.

23. The apparatus of claim 12, wherein a side of the coupling arm is configured to be substantially non-parallel to the plane of the human spinal surgical opening.

24. The apparatus of claim 12, further comprising a stabilizing device configured to couple to the frame, wherein the stabilizing device inhibits movement of the frame during use.

25. A method of retracting tissue for human spine surgery, comprising:
 preparing a human spinal surgical opening;
 retracting human tissue in the human spinal surgical opening using an apparatus, said apparatus comprising:
  a frame with an opening;
  a retainer with a straight edge and a curved edge;
  a coupling arm configured to be coupled to the frame, said coupling arm comprising a protrusion, a retainer port, a retainer port edge, and a sloped surface; and
  a retraction component configured to retract tissue in a surgical opening, said retraction component comprising a groove and a slot,
  wherein the groove slidably engages the protrusion for coupling the retraction component to the coupling arm, and the retainer is inserted into the retainer port and rotated such that the curved edge extends over the retainer port edge for securing the retraction component to the coupling arm,
  wherein when the retraction component is coupled to the coupling arm, interaction of the protrusion and the groove inhibits lateral movement and rotation of the retraction component relative to the coupling arm,
  wherein the slot of said retraction component provides a surgical instrument with access to the human spinal surgical opening, and
  wherein when the retraction component is at least partially inserted in tissue, the retraction component can be decoupled from the coupling arm and frame by rotating the retainer such that the straight edge is aligned with the retainer port edge, pulling the retraction component substantially out of an incision and substantially perpendicular to the frame opening;
 decoupling the retraction component from the coupling arm while the retraction component is at least partially inserted in tissue; and
 coupling a second retraction component to the coupling arm, said second retraction component having a length different from decoupled retraction component.

26. A method of retracting tissue for human spine surgery, comprising:
 preparing a human spinal surgical opening;
 retracting human tissue in the human spinal surgical opening using an apparatus comprising:
  a frame with an opening, wherein the frame is configured to be movably angled relative to the human spinal surgical opening;
  a retainer with a straight edge and a curved edge;
  a coupling arm configured to be coupled to the frame, said coupling arm comprising a protrusion, a retainer port, a retainer port edge, and a sloped surface; and
  a retraction component configured to retract tissue in a surgical opening, said retraction component comprising a groove and a slot,
  wherein the groove slidably engages the protrusion for coupling the retraction component to the coupling arm, and the retainer is inserted into the retainer port and rotated such that the curved edge extends over the retainer port edge for securing the retraction component to the coupling arm,
  wherein when the retraction component is coupled to the coupling arm, interaction of the protrusion and the groove inhibits lateral movement and rotation of the retraction component relative to the coupling arm,
  wherein the slot of said retraction component provides a surgical instrument with access to the human spinal surgical opening, and
  wherein when the retraction component is at least partially inserted in tissue, the retraction component can be decoupled from the coupling arm and frame by rotating the retainer such that the straight edge is aligned with the retainer port edge and pulling the retraction component substantially out of an incision and substantially perpendicular to the frame opening.

27. A method for retracting tissue for human spine surgery, comprising:
 providing a retraction apparatus to a human spinal surgical opening, the retraction apparatus comprising a frame and two or more retraction components, wherein two or more retraction components are slidably coupled to the frame and configured to retract tissue in the surgical opening and where at least one of the two or more retraction components includes a slot though which a surgical instrument is acceptable, wherein each of the two or more retraction components comprises a head and is coupled to the frame via a coupling arm and a retainer, wherein the coupling arm comprises a protrusion, a retainer port having a retainer port edge, and a sloped surface, and wherein a retraction component is coupled to the coupling arm by inserting the retainer into the retainer port and rotating the retainer such that a curved edge on the retainer extends over the retainer port edge, wherein interaction of the protrusion of the coupling arm and one or more grooves of the head of the retraction component inhibits lateral movement and rotation of the retraction component relative to the coupling arm;
 decoupling one of the retraction components from the frame by rotating the retainer such that a straight edge of the retainer is aligned with the retainer port edge, and pulling the one retraction component in a direction substantially perpendicular to the frame and out of the human spinal surgical opening while at least one retraction component remains in the surgical opening and is coupled to the frame; and
 removing the decoupled retraction component from the surgical opening while at least one retraction component remains in the surgical opening and is coupled to the frame.

28. A method for retracting tissue for human spinal surgery, comprising:
 introducing a portion of a retractor into an opening that provides access to a human spine, the retractor comprising a frame and two or more retraction components, wherein the frame is movably angled relative to the human spinal surgical opening, two or more retraction components are slidably coupled to the frame and positioned in the opening, at least one of the retractor components includes a slot through which a surgical instrument is acceptable, and at least one of the retractor components is removable from the retractor when the retractor component is positioned in the opening, wherein each of the two or more retraction components comprises a head and is coupled to the frame via a coupling arm, wherein the coupling arm comprises a protrusion, a retainer port with a port edge, and a sloped surface, and wherein a retraction component is coupled to the coupling arm by inserting a retainer into the retainer port and rotating the retainer such that a curved edge on the retainer extends over the retainer port edge, wherein interaction of the protrusion of the coupling arm and one or more grooves of the head of the retraction component inhibits lateral movement and rotation of the retraction component relative to the coupling arm;

angling the frame relative to the human spinal surgical opening; and decoupling one of the retraction components by rotating the retainer such that a straight edge of the retainer is aligned with the retainer port edge, and pulling the one retraction component in a direction substantially perpendicular to the frame and out of the opening while at least one of the retraction components is at least partially inserted in the opening.

\* \* \* \* \*